US008801686B2

(12) United States Patent
Bendele et al.

(10) Patent No.: US 8,801,686 B2
(45) Date of Patent: *Aug. 12, 2014

(54) REDUCED-PRESSURE, MULTI-ORIENTATION, LIQUID-COLLECTION CANISTER

(71) Applicant: KCI Licensing, Inc., San Antonio, TX (US)

(72) Inventors: Kevin Bendele, La Vernia, TX (US); Kenneth Smith, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/728,538

(22) Filed: Dec. 27, 2012

(65) Prior Publication Data

US 2013/0116639 A1    May 9, 2013

Related U.S. Application Data

(63) Continuation of application No. 12/973,623, filed on Dec. 20, 2010, now Pat. No. 8,377,018.

(60) Provisional application No. 61/289,938, filed on Dec. 23, 2009.

(51) Int. Cl.
    *A61M 1/00* (2006.01)
(52) U.S. Cl.
    USPC .......................................... 604/324; 604/319
(58) Field of Classification Search
    USPC ......... 604/313–315, 317–326, 403, 540–544; 215/DIG. 3; 210/644–645
    See application file for complete search history.

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 A1 | 8/1982 |
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," Current Problems in Modem Clinical Surgery: Interdepartmental Collection, edited by V. Ye Volkov et al. (Chuvashia State University, Cheboksary, U.S.S.R. 1986);pp. 94-96 (and certified translation).

(Continued)

*Primary Examiner* — Tan-Uyen T Ho
*Assistant Examiner* — Mark K Han

(57) ABSTRACT

A liquid-collection canister includes a liquid collection chamber defined by at least one wall and a first and second gas-communication pathway formed within the at least one wall. A first aperture is positioned between the first gas-communication pathway and the liquid collection chamber to allow gaseous communication between the liquid collection chamber and the first gas-communication pathway. A second aperture is positioned between the second gas-communication tion pathway and the liquid collection chamber to allow gaseous communication between the liquid collection chamber and the second gas-communication pathway. A first and a second liquid-air separator are positioned over the first aperture and the second aperture, respectively, to substantially prevent liquid passing through the first and second apertures.

8 Claims, 14 Drawing Sheets

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,719,197 A | 3/1973 | Pannier et al. |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,156,602 A | 10/1992 | Steffler |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,386,735 A | 2/1995 | Langdon |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 8,172,818 B2 * | 5/2012 | Locke et al. ............... 604/319 |
| 8,377,018 B2 * | 2/2013 | Bendele et al. ............ 604/324 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2008/0082059 A1 | 4/2008 | Fink et al. |
| 2009/0292263 A1 | 11/2009 | Hudspeth et al. |
| 2010/0063463 A1 | 3/2010 | Wiesner |

FOREIGN PATENT DOCUMENTS

| | | |
|---|---|---|
| AU | 455496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| EP | 1905465 A1 | 4/2008 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/14045 A1 | 6/1994 |
| WO | 94/20041 | 9/1994 |
| WO | 96/05873 | 2/1996 |
| WO | 97/18007 | 5/1997 |
| WO | 99/13793 | 3/1999 |
| WO | 01/24846 A1 | 4/2001 |
| WO | 01/49344 A1 | 7/2001 |
| WO | 2007/133618 A1 | 11/2007 |

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastman, RN; "When Wounds Won't Heal" RN Jan. 1998, vol. 61 (1); Medical Economics Company, Inc., Montvale, NJ, USA; pp. 20-24.

(56) References Cited

OTHER PUBLICATIONS

James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ð ukić, Ž. Maksimović, Ð . Radak, and P. Peška, "Vacuum Therapy in the Treatment of Peripheral Blood Vessels," Timok Medical Journal 11 (1986), pp. 161-164 (and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).

* cited by examiner

US 8,801,686 B2

REDUCED-PRESSURE, MULTI-ORIENTATION, LIQUID-COLLECTION CANISTER

CROSS-REFERENCE TO RELATED APPLICATIONS

This application is a continuation of Non Provisional application Ser. No. 12/973,623, filed Dec. 20, 2010, now U.S. Pat. No. 8,377,018, which claims the benefit of U.S. Provisional Application No. 61/289,938, filed Dec. 23, 2009, which is hereby incorporated by reference.

BACKGROUND OF THE INVENTION

1. Field of the Invention

The invention relates generally to reduced pressure treatment systems and more particularly to a reduced-pressure, liquid-collection canister having a filter that allows operation of the canister in multiple orientations.

2. Description of Related Art

Clinical studies and practice have shown that providing a reduced pressure in proximity to a tissue site augments and accelerates the growth of new tissue at the tissue site. The applications of this phenomenon are numerous, but one particular application of reduced pressure involves treating wounds. This treatment (frequently referred to in the medical community as "negative pressure wound therapy," "reduced pressure therapy," or "vacuum therapy") provides a number of benefits, including migration of epithelial and subcutaneous tissues, improved blood flow, and micro-deformation of tissue at the wound site. Together these benefits result in increased development of granulation tissue and faster healing times. Typically, reduced pressure is applied by a reduced pressure source to tissue through a porous pad or other manifold device. In many instances, wound exudate and other liquids from the tissue site are collected within a canister to prevent the liquids from reaching the reduced pressure source.

SUMMARY

The problems presented by existing reduced pressure systems and liquid collection canisters are solved by the systems and methods of the illustrative embodiments described herein. A liquid-collection canister for collecting liquid from a tissue site to which reduced pressure treatment is applied includes a liquid collection chamber defined by at least one wall. A first gas-communication pathway is at least partially defined by a first portion of the at least one wall, and a second gas communication pathway is at least partially defined by a second portion of the at least one wall. A first aperture is positioned between the first gas-communication pathway and the liquid collection chamber to allow gaseous communication between the liquid collection chamber and the first gas-communication pathway. A second aperture is positioned between the second gas-communication pathway and the liquid collection chamber to allow gaseous communication between the liquid collection chamber and the second gas-communication pathway. A first liquid-air separator is positioned over the first aperture to substantially prevent liquid passing through the first aperture, and a second liquid-air separator is positioned over the second aperture to substantially prevent liquid passing through the second aperture.

In another embodiment, a liquid-collection canister for collecting liquid from a tissue site is provided. The canister includes a plurality of walls forming a liquid collection chamber and a gas-communication pathway at least partially defined by a portion of a first wall and a second wall of the plurality of walls. A first aperture is positioned in the first wall between the gas-communication pathway and the liquid collection chamber, and a second aperture is positioned in the second wall between the gas-communication pathway and the liquid collection chamber. A liquid-air separator covers each of the first and second apertures.

In another embodiment, a liquid-collection canister for collecting liquid from a tissue site includes a plurality of walls forming a liquid collection chamber, each wall having an inner surface and an outer surface. A first wall of the plurality of walls includes a first recess formed in the outer surface of the first wall, and a second wall of the plurality of walls includes a second recess formed in the outer surface of the second wall. A first cover is disposed over the first recess to form a first space, and a second cover is disposed over the second recess to form a second space. A first aperture is disposed in the first wall to fluidly connect the first space and the liquid collection chamber. A second aperture is disposed in the second wall to fluidly connect the second space and the liquid collection chamber. A first liquid-air separator is positioned to substantially prevent liquid from the liquid collection chamber from entering the first space through the first aperture of the first wall, and a second liquid-air separator is positioned to substantially prevent liquid from the liquid collection chamber from entering the second space through the second aperture of the second wall. A reduced pressure port is fluidly connected to the first space and the second space.

In still another embodiment, a liquid-collection canister for collecting liquid from a tissue site to which reduced pressure treatment is applied is provided. The canister includes an outer shell and an inner liner positionable within the outer shell such that at least one gas-communication pathway is created between the inner liner and the outer shell. The inner liner defines a liquid collection chamber and further includes at least one aperture to allow gaseous communication between the liquid collection chamber and the gas-communication pathway. A liquid air separator is positioned over the at least one aperture to substantially prevent liquid passing through the aperture.

In yet another embodiment, a liquid-collection canister for collecting liquid from a tissue site to which reduced pressure treatment is applied includes a plurality of walls defining a liquid collection chamber. A fluid pathway is at least partially defined by a portion of a first wall of the plurality of walls, and the fluid pathway extends across substantially the entire width or length of the first wall. An aperture is positioned between the fluid pathway and the liquid collection chamber, and a liquid-air separator covers the first aperture to prevent the liquid from the liquid collection chamber from entering the fluid pathway.

In another embodiment, a reduced pressure treatment system for applying reduced pressure treatment to a tissue site includes a canister having a liquid collection chamber defined by at least one wall. The canister further includes a first gas-communication pathway formed within the at least one wall and a second gas communication pathway formed within the at least one wall. A first aperture is positioned between the first gas-communication pathway and the liquid collection chamber to allow gaseous communication between the liquid collection chamber and the first gas-communication pathway. A second aperture is positioned between the second gas-communication pathway and the liquid collection chamber to allow gaseous communication between the liquid collection chamber and the second gas-communication pathway. A first liquid-air separator is positioned over the first aperture to substantially prevent liquid passing through the first aperture, and a second liquid-air separator is positioned over the second aperture to substantially prevent liquid passing through the second aperture. The reduced pressure treatment system further includes a reduced pressure source in fluid communication with the canister to deliver a reduced pressure to the liquid collection chamber. The system also includes a manifold in fluid communication with the liquid collection chamber and positioned at the tissue site to distribute the reduced pressure to the tissue site.

In yet another embodiment, a reduced pressure treatment system for applying reduced pressure treatment to a tissue site includes a canister having a plurality of walls forming a liquid collection chamber. A gas-communication pathway is formed within a first wall and a second wall of the plurality of walls. A first aperture is positioned in the first wall between the gas-communication pathway and the liquid collection chamber, and a second aperture is positioned in the second wall between the gas-communication pathway and the liquid collection chamber. A liquid-air separator covers each of the first and second apertures. The system further includes a reduced pressure source in fluid communication with the canister to deliver a reduced pressure to the liquid collection chamber. The system also includes a manifold in fluid communication with the liquid collection chamber and positioned at the tissue site to distribute the reduced pressure to the tissue site.

In another embodiment, a reduced pressure treatment system having a reduced pressure source and a manifold may be paired with any of the canisters described herein.

In another embodiment, a method of collecting liquid from a tissue site includes applying a reduced pressure to a first gas-communication pathway positioned within a first side wall of a canister. The reduced pressure is applied to a second gas-communication pathway positioned within a second side wall of the canister. Gaseous flow is allowed between a liquid collection chamber of the canister and the first and second gas-communication pathways to deliver the reduced pressure to the liquid collection chamber. The method further includes drawing the liquid into the liquid collection chamber and substantially preventing the liquid from entering the first and second gas-communication pathways.

In yet another embodiment, a method of administering reduced pressure treatment to a tissue site includes applying a reduced pressure to a first gas-communication pathway positioned within a first wall of a canister. The reduced pressure is applied to a second gas-communication pathway positioned within a second wall of the canister. Gaseous flow is allowed between a liquid collection chamber of the canister and the first and second gas-communication pathways to deliver the reduced pressure to the liquid collection chamber. Reduced pressure is communicated from the liquid collection chamber to the tissue site. The method further includes drawing a liquid from the tissue site into the liquid collection chamber and substantially preventing the liquid from entering the first and second gas-communication pathways.

Other objects, features, and advantages of the illustrative embodiments will become apparent with reference to the drawings and detailed description that follow.

DETAILED DESCRIPTION OF ILLUSTRATIVE EMBODIMENTS

In the following detailed description of several illustrative embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site. Although the terms "vacuum" and "negative pressure" may be used to describe the pressure applied to the tissue site, the actual pressure reduction applied to the tissue site may be significantly less than the pressure reduction normally associated with a complete vacuum. Reduced pressure may initially generate fluid flow in the area of the tissue site. As the hydrostatic pressure around the tissue site approaches the desired reduced pressure, the flow may subside, and the reduced pressure is then maintained. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The term "tissue site" as used herein refers to a wound or defect located on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

Figure 1:
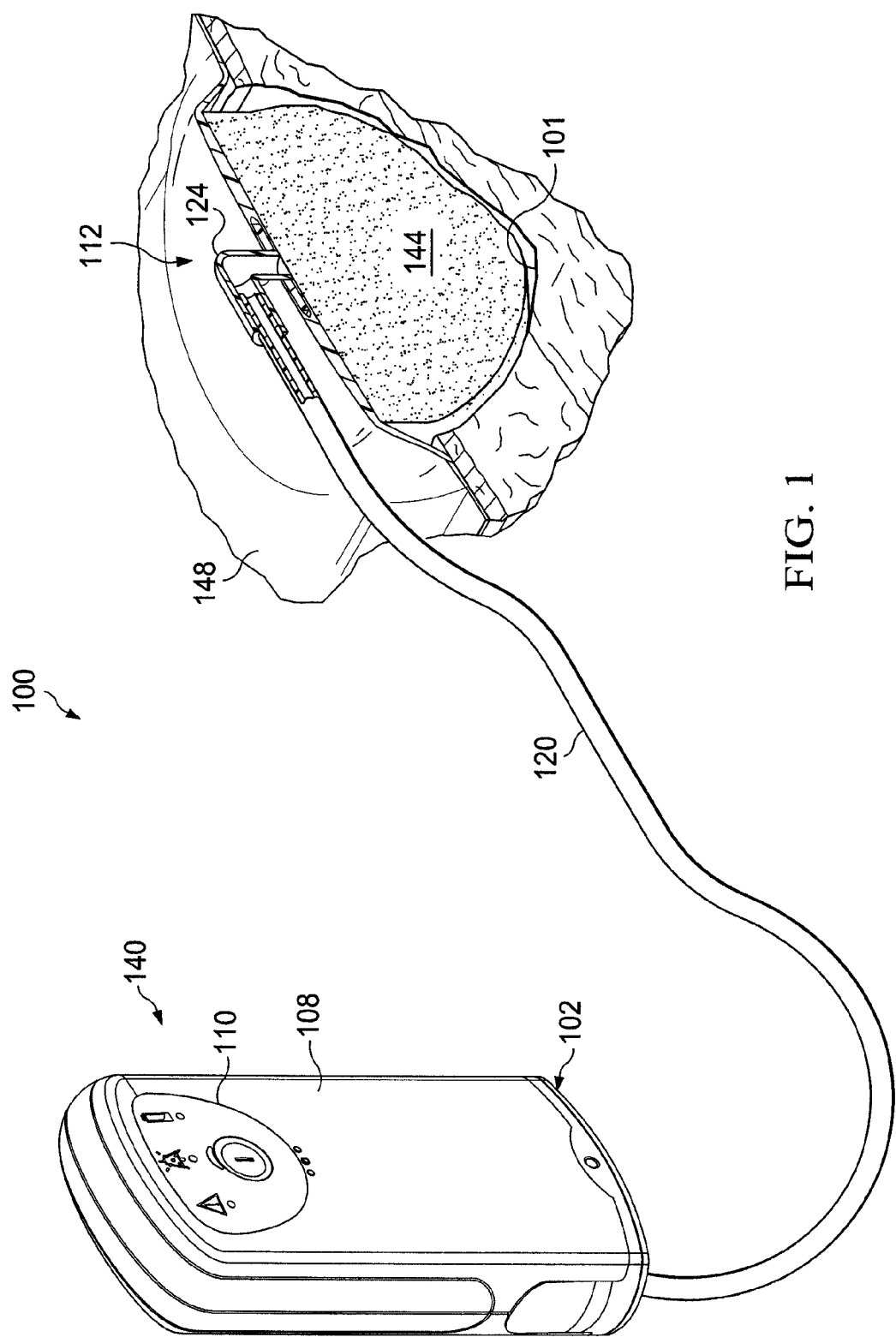
FIG. 1 illustrates a perspective view of a reduced pressure treatment system having a reduced pressure treatment unit and a multi-orientation, liquid-collection canister according to an illustrative embodiment.

Referring to FIG. 1, a reduced pressure treatment system 100 for applying a reduced pressure to a tissue site 101 of a patient according to an illustrative embodiment includes a canister 102 in fluid communication with a reduced pressure source 108 and a reduced pressure dressing 112 that is positioned at the tissue site 101. The reduced pressure dressing 112 is fluidly connected to an inlet of the canister 102 by a conduit 120. The conduit 120 may fluidly communicate with the reduced pressure dressing 112 through a tubing adapter 124.

In at least one embodiment described herein, the canister used to collect exudate or other fluids from the tissue site is configured to allow the canister to operate in multiple orientations even as the canister begins to fill with liquid. The canister preferably includes a protected gas communication pathway, or dry space, that allows continued fluid communication with a liquid collection chamber of the canister as exudate and other liquids collect within the liquid collection chamber. The path of fluid communication in the reduced pressure treatment system is as follows. Reduced pressure is supplied to the gas communication pathway of the canister by the reduced pressure source. Typically this occurs by the reduced pressure source drawing gaseous fluids, such as air, from the gas communication pathway. As the pressure within the gas communication pathway falls, gas flows from the liquid collection chamber of the canister to the gas communication pathway, thus resulting in a drop in pressure within the liquid collection chamber. Liquid is prevented from flowing into the gas communication pathway by a hydrophobic element, an oleophobic element, or some other type of liquid-blocking membrane or device. The reduced pressure within the liquid collection chamber is transmitted to the dressing at the tissue site, which allows fluids (both gases and liquids) to flow from the tissue site to the liquid collection chamber. The liquid collects within the liquid collection chamber. Multiple fluid communication ports between the liquid collection chamber and the gas communication pathway allow continued gaseous communication between the liquid collection chamber and the gas communication pathway even as the liquid collection chamber fills with liquids and blocks some of these communication ports. This configuration permits continued supply of reduced pressure to the liquid collection chamber until the liquid collection canister is almost completely full of liquid. As an alternative to the multiple ports, a large common port may be provided so that only a portion of the port is covered or blocked by liquid as the canister fills.

In the embodiment illustrated in FIG. 1, the reduced pressure source 108 is an electrically-driven vacuum pump. In another implementation, the reduced pressure source 108 may instead be a manually-actuated or manually-charged pump that does not require electrical power. The reduced pressure source 108 instead may be any other type of reduced pressure pump, or alternatively a wall suction port such as those available in hospitals and other medical facilities. The reduced pressure source 108 may be housed within or used in conjunction with a reduced pressure treatment unit 140, which may also contain sensors, processing units, alarm indicators, memory, databases, software, display units, and user interfaces 110 that further facilitate the application of reduced pressure treatment to the tissue site 101. In one example, a sensor or switch (not shown) may be disposed at or near the reduced pressure source 108 to determine a source pressure generated by the reduced pressure source 108. The sensor may communicate with a processing unit that monitors and controls the reduced pressure that is delivered by the reduced pressure source 108.

The reduced pressure dressing 112 includes a distribution manifold 144 adapted to be positioned at the tissue site 101, and a cover 148, or drape, that is positioned over the distribution manifold 144 to maintain reduced pressure beneath the cover 148 at the tissue site 101. The cover 148 may extend beyond a perimeter of the tissue site 101 and may include an adhesive or bonding agent on the cover 148 to secure the cover to tissue adjacent the tissue site 101. In one embodiment, the adhesive disposed on cover 148 may be used to seal between the tissue and the cover 148 to prevent leakage of reduced pressure from the tissue site 101. In another embodiment, a seal layer (not shown) such as, for example, a hydrogel or other material may be disposed between the cover 148 and the tissue to augment or substitute for the sealing properties of the adhesive.

The distribution manifold 144 of the reduced pressure dressing 112 is adapted to contact the tissue site 101. The distribution manifold 144 may be partially or fully in contact with the tissue site 101 being treated by the reduced pressure dressing 112. When the tissue site 101 is a wound, the distribution manifold 144 may partially or fully fill the wound.

The distribution manifold 144 may be any size, shape, or thickness depending on a variety of factors, such as the type of treatment being implemented or the nature and size of the tissue site 101. For example, the size and shape of the distribution manifold 144 may be customized by a user to cover a particular portion of the tissue site 101, or to fill or partially fill the tissue site 101. The distribution manifold 144 may have, for example, a square shape, or may be shaped as a circle, oval, polygon, an irregular shape, or any other shape.

In one illustrative embodiment, the distribution manifold 144 is a foam material that distributes reduced pressure to the tissue site 101 when the distribution manifold 144 is in contact with or near the tissue site 101. The foam material may be either hydrophobic or hydrophilic. In one non-limiting example, the distribution manifold 144 is an open-cell, reticulated polyurethane foam such as GranuFoam® dressing available from Kinetic Concepts, Inc. of San Antonio, Tex.

In the example in which the distribution manifold 144 is made from a hydrophilic material, the distribution manifold 144 also functions to wick fluid away from the tissue site 101, while continuing to provide reduced pressure to the tissue site 101 as a manifold. The wicking properties of the distribution manifold 144 draw fluid away from the tissue site 101 by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The distribution manifold 144 may further promote granulation at the tissue site 101 when a reduced pressure is applied through the reduced pressure dressing 112. For example, any or all of the surfaces of the distribution manifold 144 may have an uneven, coarse, or jagged profile that causes microstrains and stresses at the tissue site 101 when reduced pressure is applied through the distribution manifold 144. These microstrains and stresses have been shown to increase new tissue growth.

In one embodiment, the distribution manifold 144 may be constructed from bioresorbable materials that do not have to be removed from a patient's body following use of the reduced pressure dressing 112. Suitable bioresorbable materials may include, without limitation, a polymeric blend of polylactic acid (PLA) and polyglycolic acid (PGA). The polymeric blend may also include without limitation polycarbonates, polyfumarates, and capralactones. The distribution manifold 144 may further serve as a scaffold for new cell-growth, or a scaffold material may be used in conjunction with the distribution manifold 144 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

Figure 7:
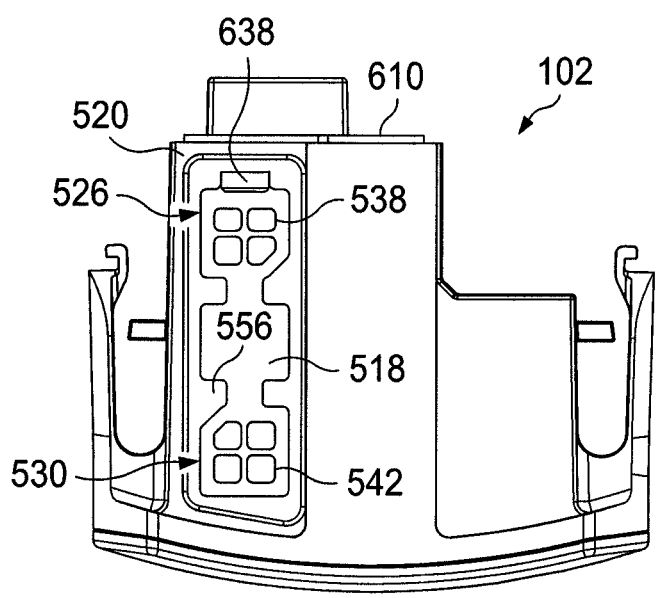
FIG. 7 illustrates a rear view of the liquid-collection canister of FIG. 4.
Figure 8:
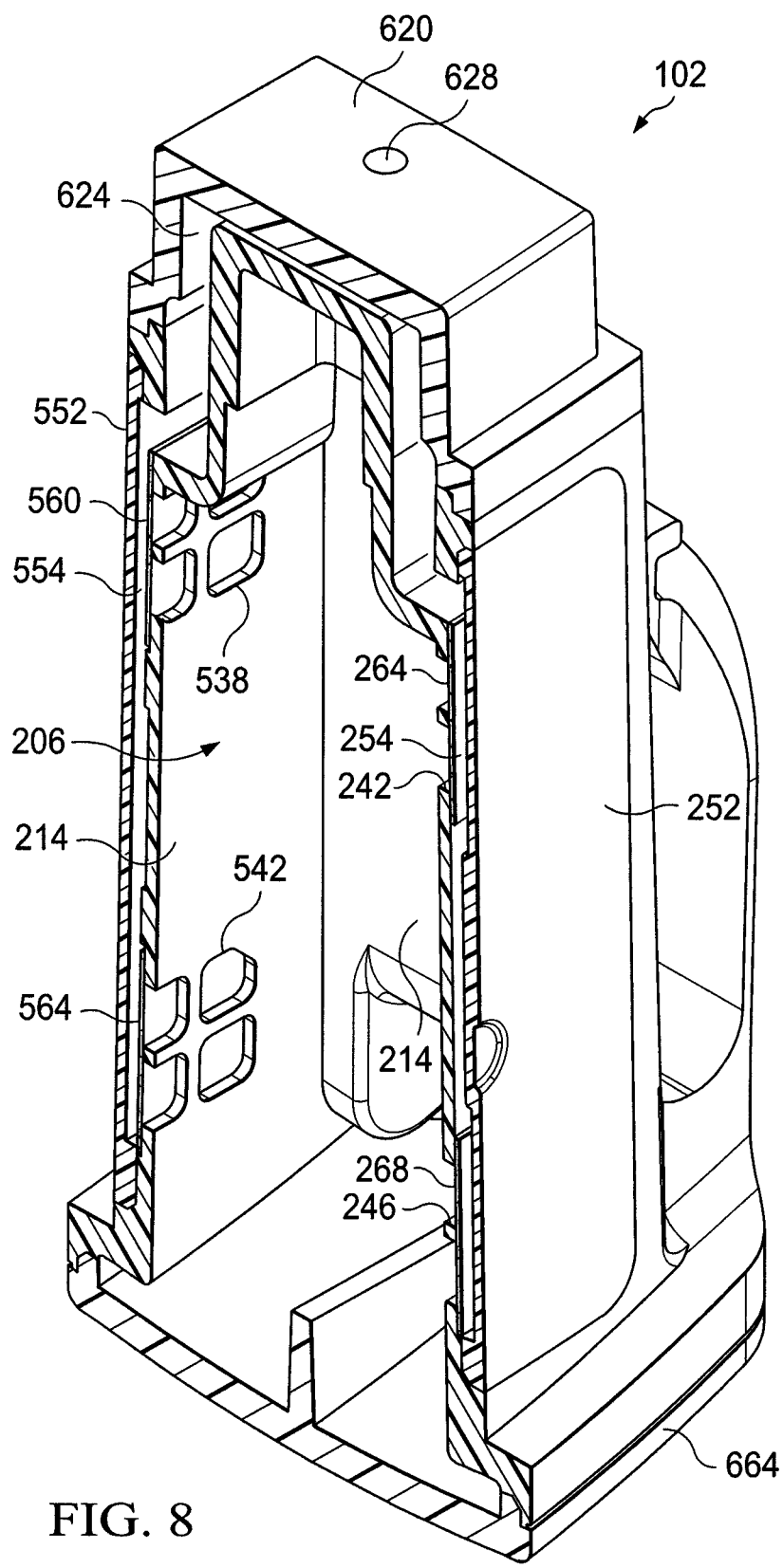
FIG. 8 illustrates a perspective cross-sectional view of the liquid-collection canister of FIG. 2 taken at 8-8.

Referring still to FIG. 1, but also to FIGS. 2-8, the canister 102 includes a plurality of walls 202 to form a liquid collection chamber 206 (see FIG. 8). Each of the plurality of walls 202 includes an outer surface 210 and an inner surface 214. In one embodiment, a recess 218 is formed in the outer surface 210 of a wall 220 of the plurality of walls 202. The recess 218 may be substantially L-shaped and include a first leg portion 226 and a second leg portion 230, the first and second leg portions 226, 230 intersecting at an apex region 234. A plurality of apertures 238 is positioned at an end of the first leg portion 226 opposite the apex region 234, and another plurality of apertures 242 is positioned at an end of the second leg portion 230 opposite the apex region 234. A plurality of apertures 246 may also be positioned in the apex region 234. Each of the plurality of apertures 238, 242, 246 is illustrated as including four apertures, but it should be noted that any number of apertures, including a single aperture, could be provided.

The recess 218 is capable of being covered by a cover 252 to create a space 254 (see FIG. 8) between the cover 252 and the wall 220 of the canister 102. While the cover 252 could be attached directly to the outer surface 210 of the wall 220, in one embodiment, a raised flange 256 may be provided within the recess 218 on which the cover 252 may be positioned. By positioning the cover 252 within the recess 218, the cover 252 is capable of being flush with the outer surface 210. By providing the raised flange 256 on which the cover 252 may rest, the space 254 between the cover 252 and the wall 220 is maintained to provide a gas-communication pathway within the wall 220. The cover 252 and the walls 202 of the canister 102 may be made from a plastic, thermoplastic, thermoset, fiber-type material, ceramic, metal, or any other material that is capable of maintaining a desired shape under the influence of a reduced pressure and that is capable of being exposed to wound fluids or other liquids. The cover 252 may be adhesively bonded, welded, or attached in any other suitable manner to the wall 220. Preferably, the means of attachment will provide a substantially gas impermeable seal between the cover 252 and the wall 220 such that reduced pressure may be delivered through the gas-communication pathway (i.e. the space 254) within the wall 220 without leakage between the cover 252 and wall 220. While the space 254 is positioned within the wall 220 by providing the recess 218 and cover 252, in another embodiment, the space 254 may be integrally formed within the wall 220 without the use of a cover 252. For example, the space 254 could be integrally molded within the wall 220 during construction of the canister 102. When the spaces or gas-communication pathways described herein are referred to as being formed or positioned "within" a wall, it is to be understood that the space or gas-communication pathway may be integrally formed within the wall during construction, formed after construction of the wall by any suitable manufacturing technique, or formed within a recess or other depression that is then bordered on one or more sides by a cover.

The apertures 238, 242, 246 positioned within the recess 218 allow fluid communication between the liquid collection chamber 206 and the space 254. A liquid-air separator 260, 264, 268 is positioned over each of the plurality of apertures 238, 242, 246. In one illustrative embodiment, the liquid-air separators are hydrophobic membranes or material that allow the transmission of gases but substantially prevent the transmission of liquids through the liquid-air separator. Instead of the liquid-air separators being made from a hydrophobic material, the liquid-air separators may be a gas permeable material that is coated with a hydrophobic substance to make the material substantially impermeable to liquid. In one embodiment, the liquid-air separator may be a chemically bonded fluorocarbon monomer using a plasma process, thus increasing the hydrophobicity of the liquid-air separator. The liquid-air separators may also be oleophobic or lipophobic, or coated with an oleophobic or lipophobic substance. The oleophobicity or lipophobicity of the liquid-air separator contributes to the ability of the liquid-air separator to wick or shed exudate and other wound fluids if the liquid-air separator is incidentally contacted by the liquid. Some exemplary materials that may be used as liquid-air separators include, without limitation, expanded polytetrafluoroethylene (ePTFE), polytetrafluoroethylene (PTFE), foam, spun fiberglass, cotton gauze, polyester, glass fibers, polypropylene, microfibers, porous polymeric membranes, or any other materials or substances that are hydrophobic, oleophobic, or lipophobic in nature.

Figure 5:
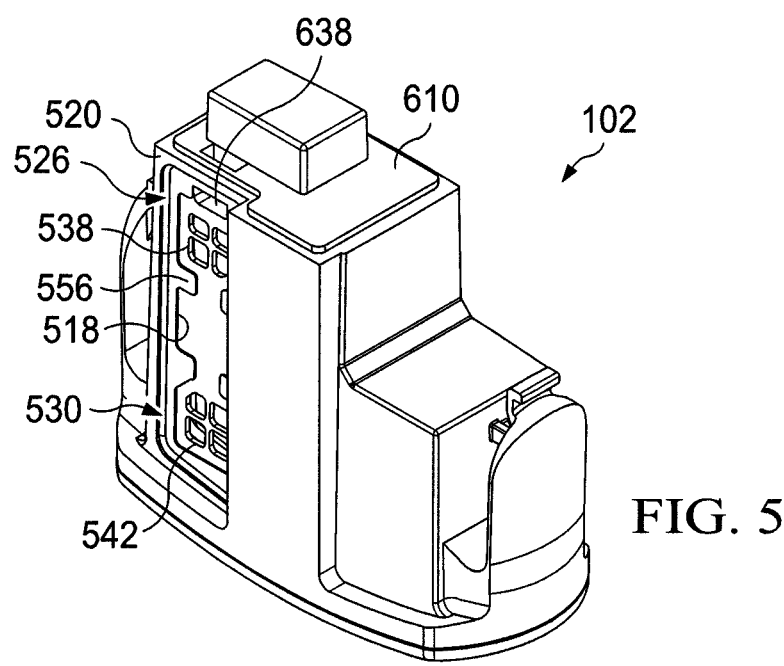
FIG. 5 illustrates a rear perspective view of the liquid-collection canister of FIG. 4.
Figure 6:
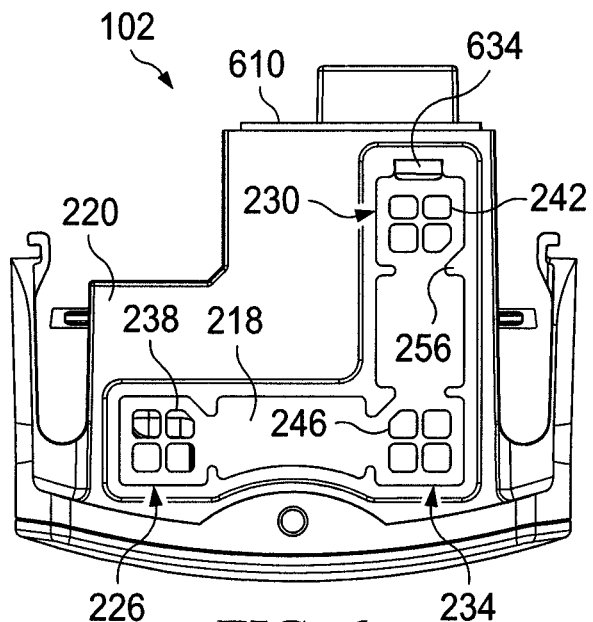
FIG. 6 illustrates a front view of the liquid-collection canister of FIG. 4.

Referring more specifically to FIGS. 5, 7, and 8, a recess 518 is formed in the outer surface 210 of a wall 520 of the plurality of walls 202. The recess 518 may be substantially rectangular in shape and include a first end 526 and a second end 530. A plurality of apertures 538 is positioned at the first end 526 of the recess 518, and a plurality of apertures 542 is positioned at a second end 530 of the recess 518. Similar to the apertures 238, 242, 246 of recess 218, each of the plurality of apertures 538, 542 is illustrated as including four apertures. It should be noted, however, that any number of apertures, including a single aperture, could be provided.

The recess 518 may be covered by a cover 552 to create a space 554 (see FIG. 8) between the cover 552 and the wall 520 of the canister 102. While the cover 552 could be attached directly to the outer surface 210 of the wall 520, in one embodiment, a raised flange 556 may be provided within the recess 518 on which the cover 552 may be positioned. By positioning the cover 552 within the recess 518, the cover 552 is capable of being flush with the outer surface 210 of the wall 520. The raised flange 556 on which the cover 552 may rest, maintains the space 554 between the cover 552 and the wall 520 to provide a gas-communication pathway within the wall 520. Similar to cover 252, cover 552 may be adhesively bonded, welded, or attached in any other suitable manner to the wall 520. Preferably, the means of attachment will provide a substantially gas impermeable seal between the cover 552 and the wall 520 such that reduced pressure may be delivered through the gas-communication pathway (i.e. the space 554) within the wall 520 without leakage between the cover 552 and wall 520. While the space 554 is positioned within the wall 520 by providing the recess 518 and cover 552, alternatively, the space 554 may be integrally formed in the wall 520 such as by molding or any other suitable manufacturing technique.

The apertures 538, 542 positioned within the recess 518 allow fluid communication between the liquid collection chamber 206 and the space 554. A liquid-air separator 560, 564 is positioned over each of the plurality of apertures 538, 542. The liquid-air separators 560, 564 may be similar in material and construction to liquid-air separators 260, 264, 268.

Referring more specifically to FIGS. 3-5 and 8, a wall 610 of the plurality of walls 202 is positioned between and adjoins wall 220 and wall 520. A cap 620 is positioned above the outer surface 210 of the wall 610 to create a manifold chamber 624 (see FIG. 8) between the outer surface 210 of the wall 610 and the cap 620. The cap includes at least one reduced pressure port 628 to allow fluid communication between the reduced pressure source 108 and the manifold chamber 624. Additional ports may be provided in cap 620 to provide additional fluid communication with manifold chamber 624. In one example, a second port may be included to allow communication with a pressure sensor used to measure the amount of pressure associated with the canister 102. The cap 620 may be joined to the wall 610 using means similar to that used to join the covers 252, 552 to the walls 220, 520.

The canister 102 further includes a passage 634 that allows fluid communication between the space 254 and the manifold chamber 624. Similarly, a passage 638 is provided to permit fluid communication between the space 554 and the manifold chamber 624. Each of the passages 634, 638 is integrally formed within the walls 202 without penetrating the liquid collection chamber 206.

Figure 3:
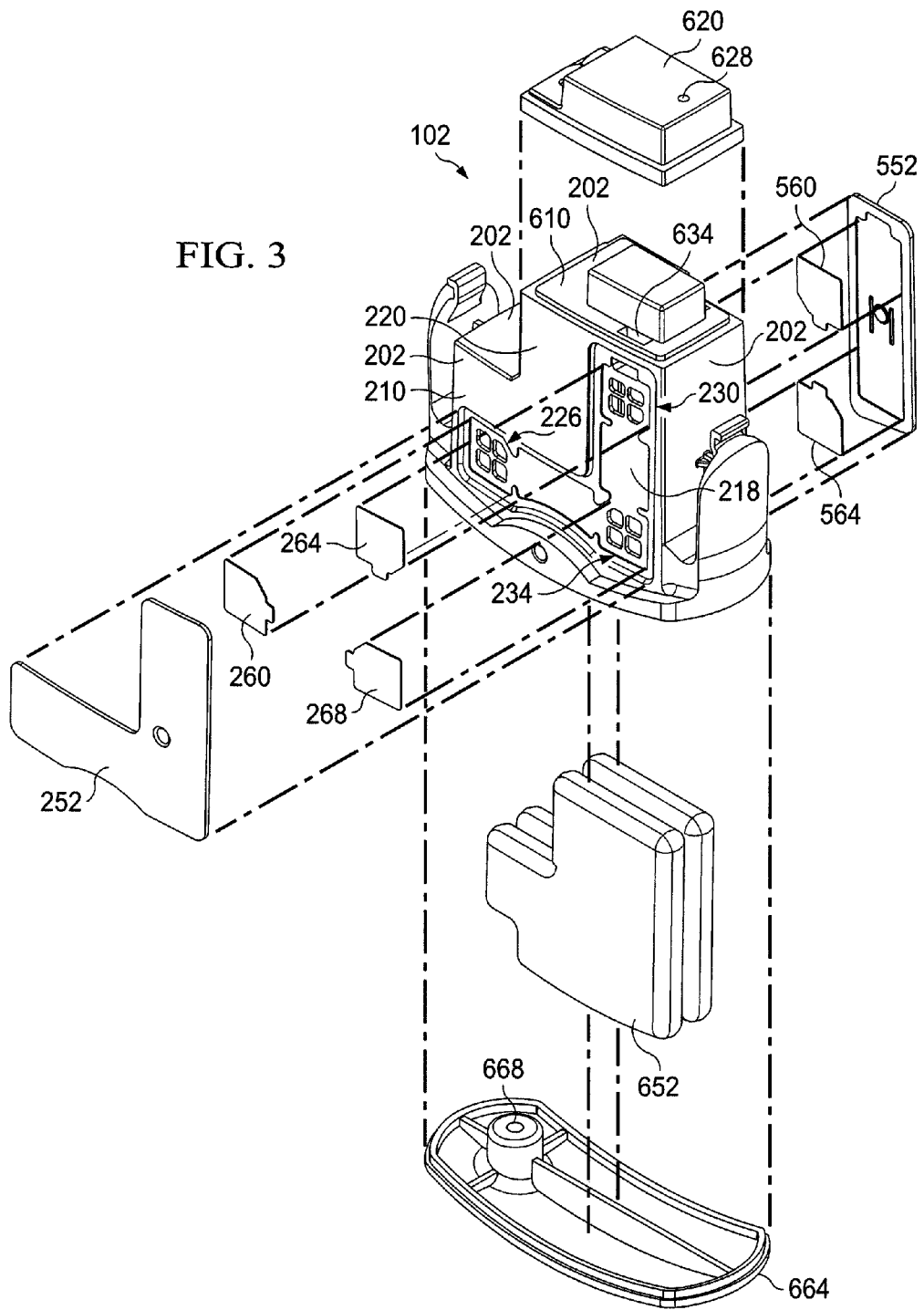
FIG. 3 illustrates an exploded perspective view of the liquid-collection canister of FIG. 1.
Figure 4:
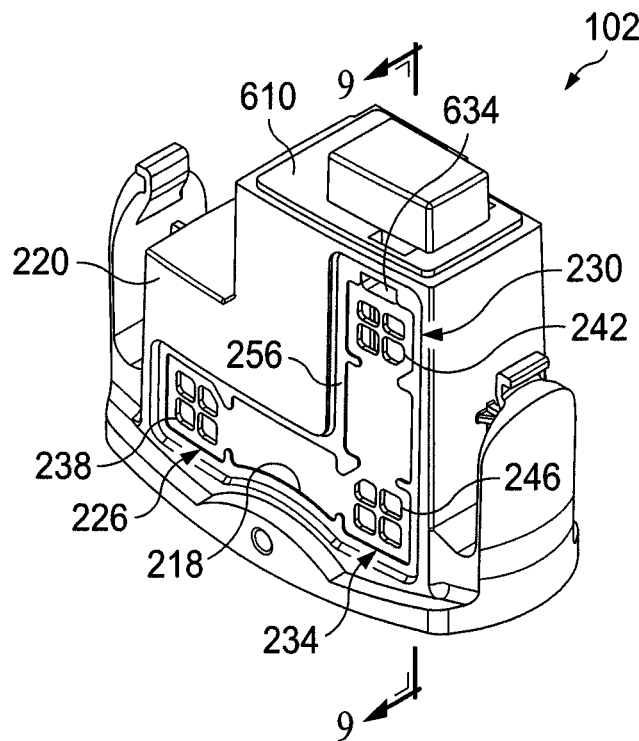
FIG. 4 illustrates a front perspective view of the liquid-collection canister of FIG. 3 with covers and filter elements associated with the liquid-collection canister being removed.

Referring still to FIG. 3, the canister 102 may further include one or more absorbent pads 652 positioned in the liquid collection chamber 206 to absorb liquid collected drawn into the liquid collection chamber 206 from the tissue site 101. The absorbent pads 652 preferably include cellulose and sodium polyacrylate contained within a non-woven polypropylene pouch. Alternatively, the absorbent pads 652 could be made from any absorbent, adsorbent, or desiccant material or substance. By capturing liquid, the absorbent pads 652 prevent sloshing of the liquid in the chamber and premature wetting of the liquid-air separators.

A lower lid 664 is provided to enclose the absorbent pads 652 within the liquid collection chamber 206. While the lower lid could be removably attached to walls 202, in another embodiment, the lower lid is permanently affixed to the walls 202 in a manner similar to that used to attach covers 252, 552 and cap 620. The lower lid 664 includes an inlet port 668 that permits attachment of conduit 120.

Figure 2:
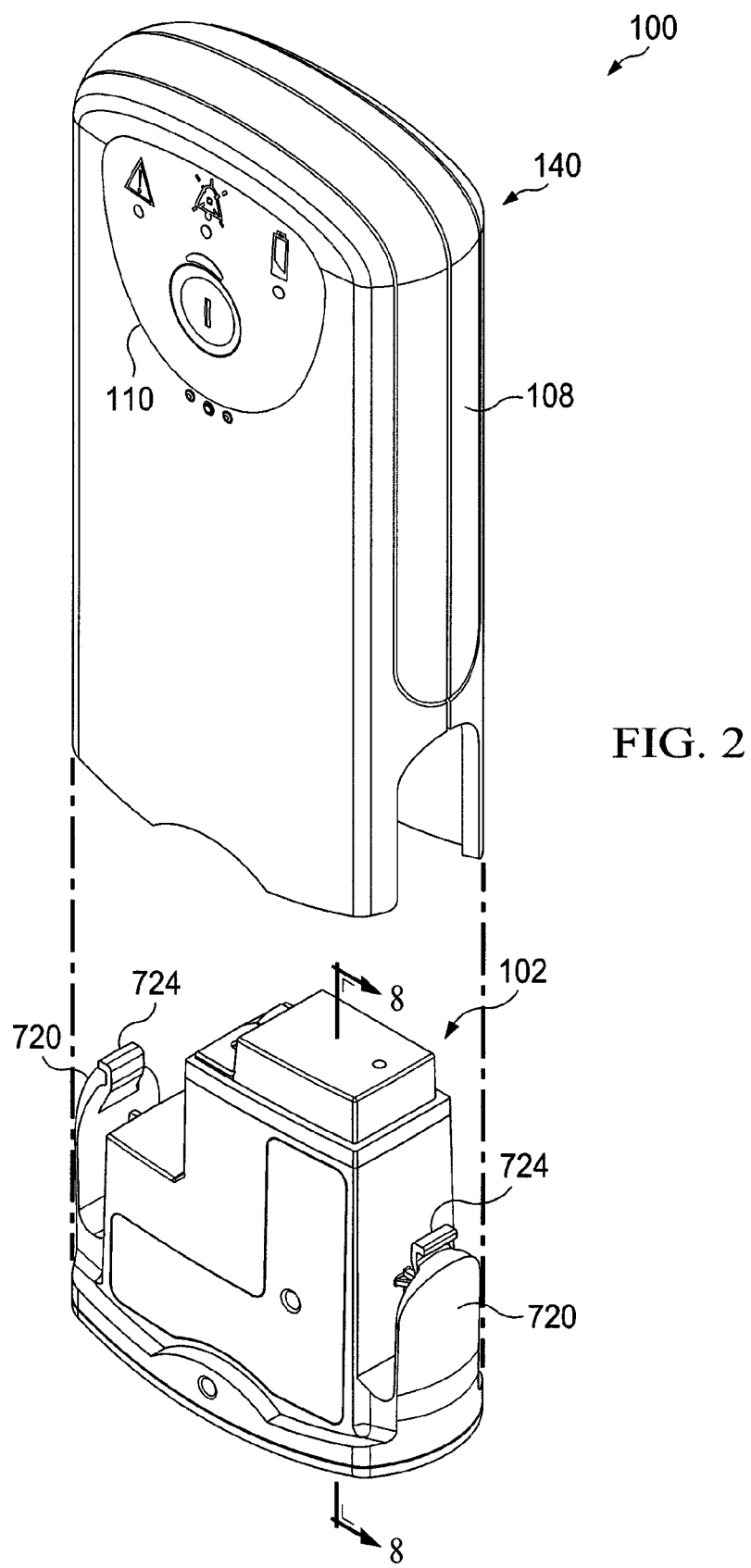
FIG. 2 illustrates an exploded perspective view of the reduced pressure treatment unit and liquid-collection canister of FIG. 1.

Referring still to FIG. 3, but also again to FIG. 2, the canister 102 may be removable from reduced pressure therapy unit 140. The canister 102 may include a pair of attachment tabs 720 having locking clips 724 that serve to removably secure the canister 102 to mating detents or hardware within the therapy unit 140. Removal of the canister 102 is accomplished by simultaneously exerting inward forces upon the attachment tabs 720 and pulling the canister 102 away from the therapy unit 140. Removal of the canister 102 allows the canister 102 to be replaced with a new canister when the canister 102 has become full of wound exudate or other liquid collected from the tissue site 101.

The shape and positioning of the walls 202 of the canister 102 could vary depending on the shape and size of the therapy unit 140. In some embodiments, it may be desired to use a stand-alone canister that is not secured to a therapy unit, but rather that is only fluidly connected to a therapy unit or reduced pressure source by a conduit or other pathway. While the walls 202 of the canister illustrated in FIGS. 2-8 are substantially planar and are arranged substantially perpendicular to adjacent walls, the walls could instead be non-planar and could in some embodiments be positioned at non-perpendicular angles relative to adjacent walls. In another embodiment, a lesser number of walls may be provided such as, for example, in a configuration that includes a cylindrically or spherically shaped wall. In such a configuration, one or more spaces or gas-communication pathways may be formed in the cylindrically or spherically shaped wall. One or more apertures may be provided to communicate with the one or more spaces in the cylindrical or spherical wall, and the one or more apertures may be covered by one or more liquid-air separators.

In the embodiment illustrated in FIGS. 2-8, the spaces 254, 554 or gas-communication pathways are illustrated in walls 220, 520, and the walls 220, 520 are opposite one another. In an alternative embodiment, the walls containing the gas-communication pathways may be adjacent one another. In the case of an irregularly-shaped canister, the walls containing gas-communication pathways may not be adjacent or opposite one another. While illustrated in FIGS. 2-8 with only one space 254, 554 per wall 220, 520, multiple, independent spaces or gas-communication pathways could be included within a particular wall of the canister. Each of the spaces may communicate with a common plenum, such as manifold chamber 624, or the individual spaces may be separately ducted to a common conduit or directly to reduced pressure source 108. The canister 102 illustrated in FIGS. 2-8 includes two walls having spaces 254, 554. The number of walls having spaces or gas-communication pathways is not limited. Such pathways may be provided in only one wall or may be present in all walls of the canister. Similarly, the number of apertures providing fluid communication between a gas-communication pathway and the liquid collection chamber is not strictly limited. In some embodiments, multiple apertures may be provided and spaced apart within the gas-communication pathway to permit more efficient collection and utilization of the liquid collection chamber as described in more detail below.

In operation, wound exudate and other liquids are drawn from the tissue site 101 by the reduced pressure source. The liquids travel through conduit 120 and into the liquid collection chamber 206 through the inlet port 668 of the lower lid 664. The liquid collection chamber 206 of the canister 102 forms a first space where liquid from the tissue site 101 is collected. The spaces 254, 554, or gas-communication pathways, are dry spaces that are substantially protected from liquid by the liquid-air separators 260, 264, 268, 560, 564.

The spaces 254, 554 allow the passage of gas as reduced pressure is applied by the reduced pressure source 108 gases are drawn from the liquid collection chamber 206 and the tissue site 101. As the pressure at the tissue site 101 and within the liquid collection chamber 206 approach the desired amount of reduced pressure required for therapy, the flow of gases through the liquid collection chamber 206 and the spaces 254, 554 is reduced, but liquid may continue to be drawn from the tissue site 101 and collected in the liquid collection chamber 206.

Figure 9:
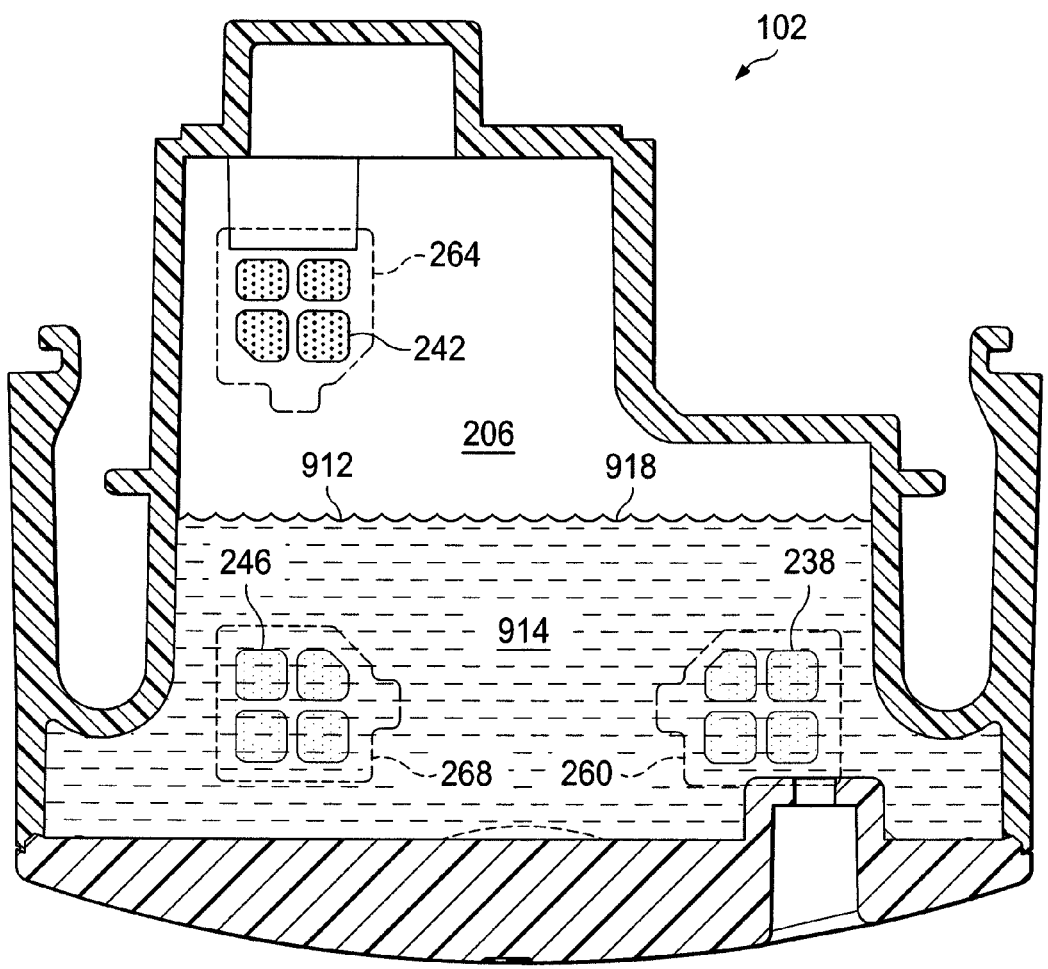
FIG. 9 illustrates a cross-sectional view of the liquid-collection canister of FIG. 4 taken at 9-9, the liquid-collection canister shown containing a liquid.

Referring to FIG. 9, which represents a cross-sectional view of the canister 102 with an orientation similar to that of FIG. 7, a liquid line 912 represents an upper surface of liquid 914 that is collected within the liquid collection chamber 206. As the liquid 914 fills the liquid collection chamber 206, the liquid 914 is substantially prevented from passing through the liquid-air separators 260, 264, 268 to enter the space 254 within wall 220. The surface of the liquid 914 represented by liquid line 912 is substantially planar and forms a liquid plane 918. As the liquid 914 rises within the canister 102, any portion of the liquid-air separators 260, 264, 268 below the surface of the liquid 914 will no longer allow transmission or flow of gas between the liquid collection chamber 206 and the space 254. In other words, the reduced pressure will no longer be delivered or transferred to the liquid collection chamber 206 through the portion of the liquid-air separators 260, 264, 268 that is covered in liquid 914. In FIG. 9, only liquid-air separator 264 is above the surface of the liquid 914, therefore, gas transmission between the liquid collection chamber 206 and the space 254 occurs only through plurality of apertures 242. As long as a portion of the liquid-air separator 264 remains uncovered by liquid 914, the liquid-air separator 264 will continue to permit gas flow and transmission of reduced pressure.

Because a cross-sectional view is illustrated in FIG. 9, the apertures 538, 542 and liquid-air separators 560, 564 associated with wall 520 are not depicted. However, given the orientation of the canister in FIG. 9, only liquid-air separator 560 is above the surface of the liquid 914. Consequently, liquid-air separator 560 continues to allow gas to travel through the apertures 538 between liquid collection chamber 206 and space 554. Liquid-air separator 564 is below the surface of the liquid 914 and in this position no longer allows passage of gas through the apertures 542.

Figure 10:
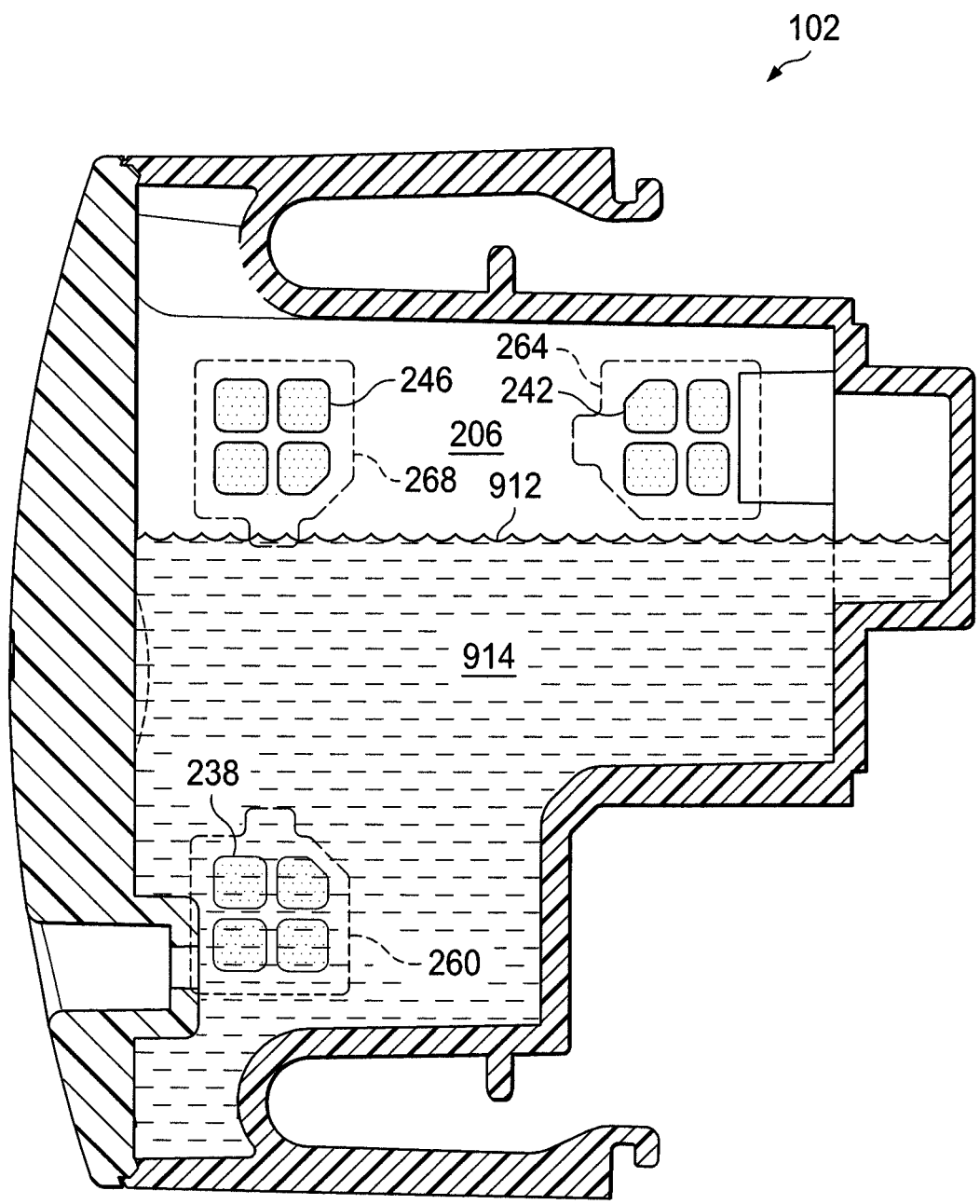
FIG. 10 illustrates a cross-sectional view of the liquid-collection canister of FIG. 9 rotated ninety degrees clockwise.

Referring to FIG. 10, which represents a cross-sectional view of the canister 102 similar to that of FIG. 9 but with the canister rotated ninety degrees clockwise, liquid-air separator 260 is below the surface of the liquid 914 and thus is not capable of transmitting gas from the liquid collection chamber 206 to the space 254. Liquid-air separators 264, 268, however, are both above the surface of the liquid 914 and continue to allow communication of gaseous flow between the liquid collection chamber 206 and the space 254 through apertures 242, 246. Although not depicted in FIG. 10, the orientation of the canister 102 in this figure results in both of the liquid-air separators 560, 564 associated with wall 520 being located above the surface of the liquid 914. This orientation permits gaseous communication through these liquid-air separators 560, 564.

Figure 11:
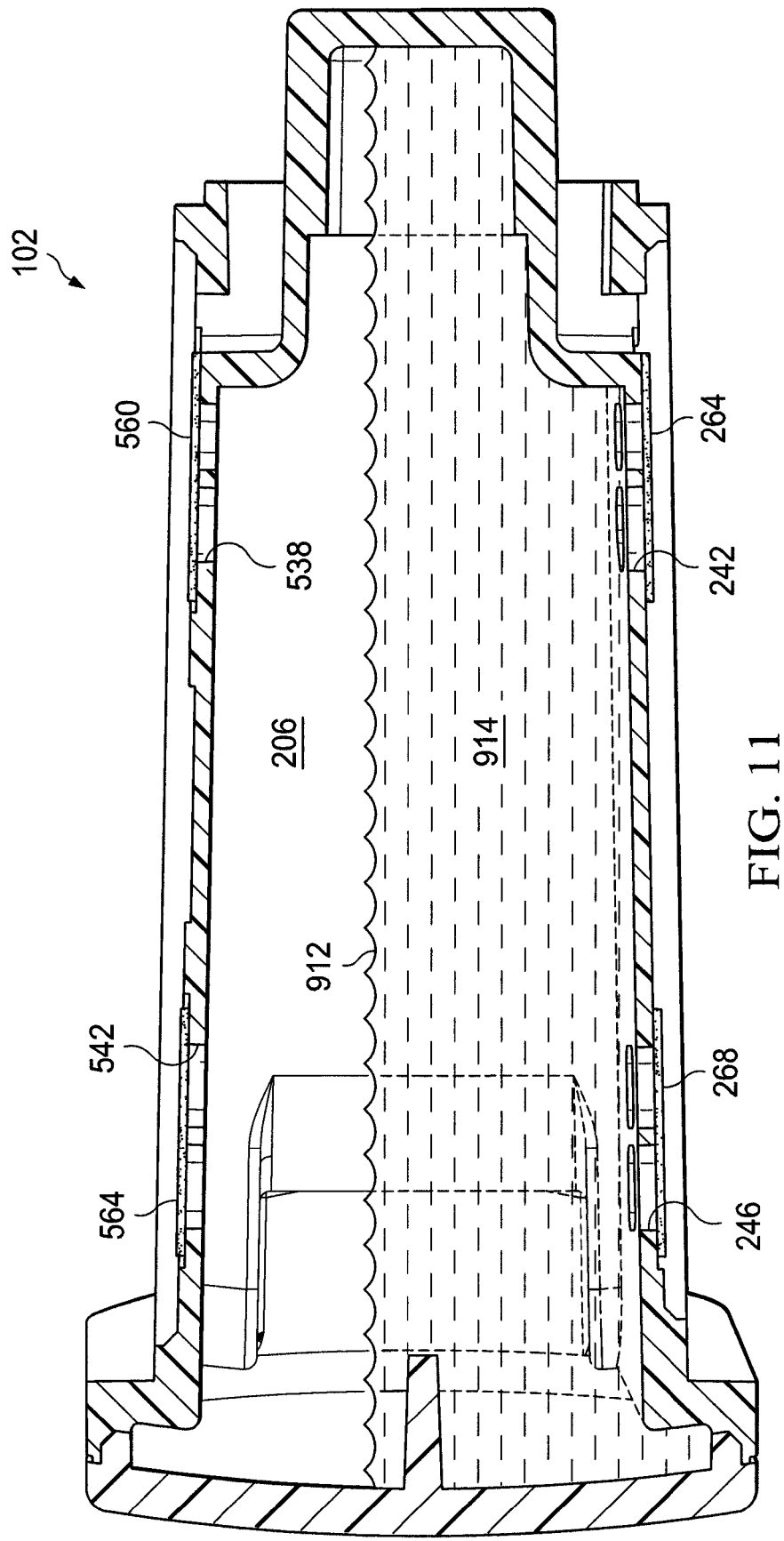
FIG. 11 illustrates a cross-sectional view of the liquid-collection canister similar to that of FIG. 8, but rotated ninety degrees clockwise, the liquid-collection canister shown containing a liquid.

Referring to FIG. 11, another orientation of the canister is illustrated 102 similar to the cross-section shown in FIG. 8 but rotated ninety degrees clockwise. In this particular orientation, all of the liquid-separators 260, 264, 268 associated with wall 220 are beneath the surface of the liquid 914, thereby preventing gaseous flow between the liquid collection chamber 206 and the space 254 through apertures 238, 242, 246. In contrast, both of the liquid-air separators 560, 564 associated with wall 520 are above the surface of the liquid and are therefore capable of allowing gaseous flow through apertures 538, 542.

It is important to note that in each of the orientations of the canister 102 shown in FIGS. 9-11, as well as in additional orientations of the canister 102 that have not been illustrated, the shape, size and relative positioning of the liquid-air separators allow the canister to continue to transmit reduced pressure even as the level of liquid 914 within the canister 102 rises to and beyond the volume of the liquid collection chamber 206 being half full of liquid. This multi-orientation capability of the canister 102 is not available with many liquid-collection canisters, especially those canisters that include a single filter element or multiple filter elements that are all arranged in a co-planar arrangement. With these types of filters, a particular orientation of the filter (usually the orientation that results in the planar filter element being positioned at the bottom of the canister) will allow only a small amount of liquid collection. As the liquid covers the filter element completely, flow of gas and thus transmission of reduced pressure through the canister ceases.

The success of the canister 102 at allowing large volumes of liquid to be collected in any orientation of the canister 102 is due in part to the placement of gas communication pathways within or along multiple walls of the canister 102 and providing at least one liquid-air separator on each of those walls. While it is not necessary, or may not be desired for reasons of cost, to have a liquid-air separator on each wall of the canister, the presence of liquid air separators on opposing walls of the canister, such as in the configuration shown in FIGS. 3-9, provides efficient collection of large volumes of liquid even when one of the liquid-air-separator-containing walls is oriented downward such as is illustrated in FIG. 11. By providing multiple liquid-air separators on each wall that includes liquid-air separators, the ability to collect higher volumes of liquid is increased when one of the liquid-air-separator-containing walls is oriented in an upright position such as is shown in FIGS. 9 and 10. It should be noted that as a substitute for multiple liquid-air separators on a particular wall, a large liquid-air separator may be provided that covers an aperture or apertures having greater surface area. This may not always be preferred, however, due to high costs associated with the materials sometimes used for liquid-air separators.

Figure 12:
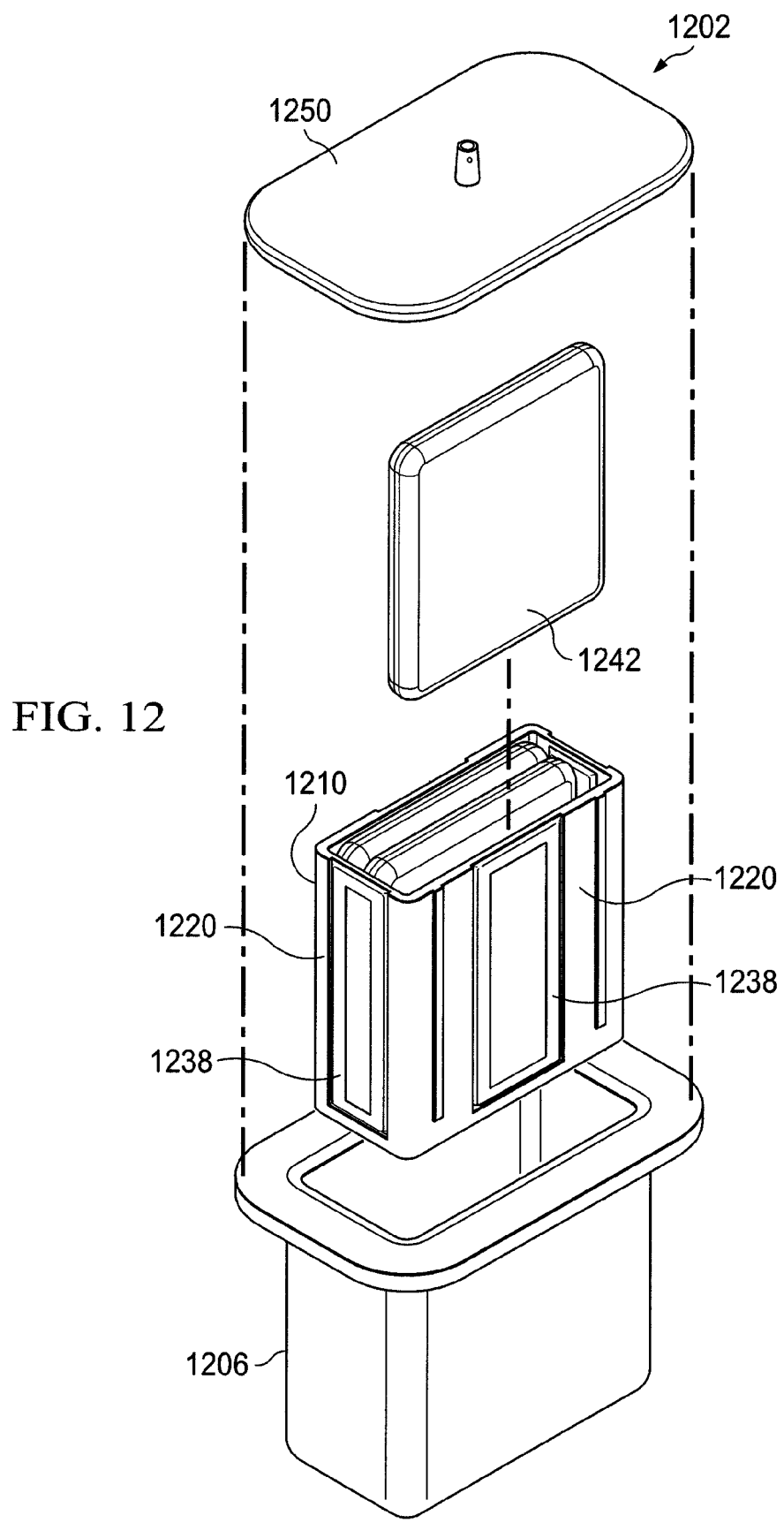
FIG. 12 illustrates an exploded perspective view of a reduced pressure treatment system having a multi-orientation, liquid-collection canister according to an illustrative embodiment, the liquid-collection canister having an outer shell and an inner liner.
Figure 13:
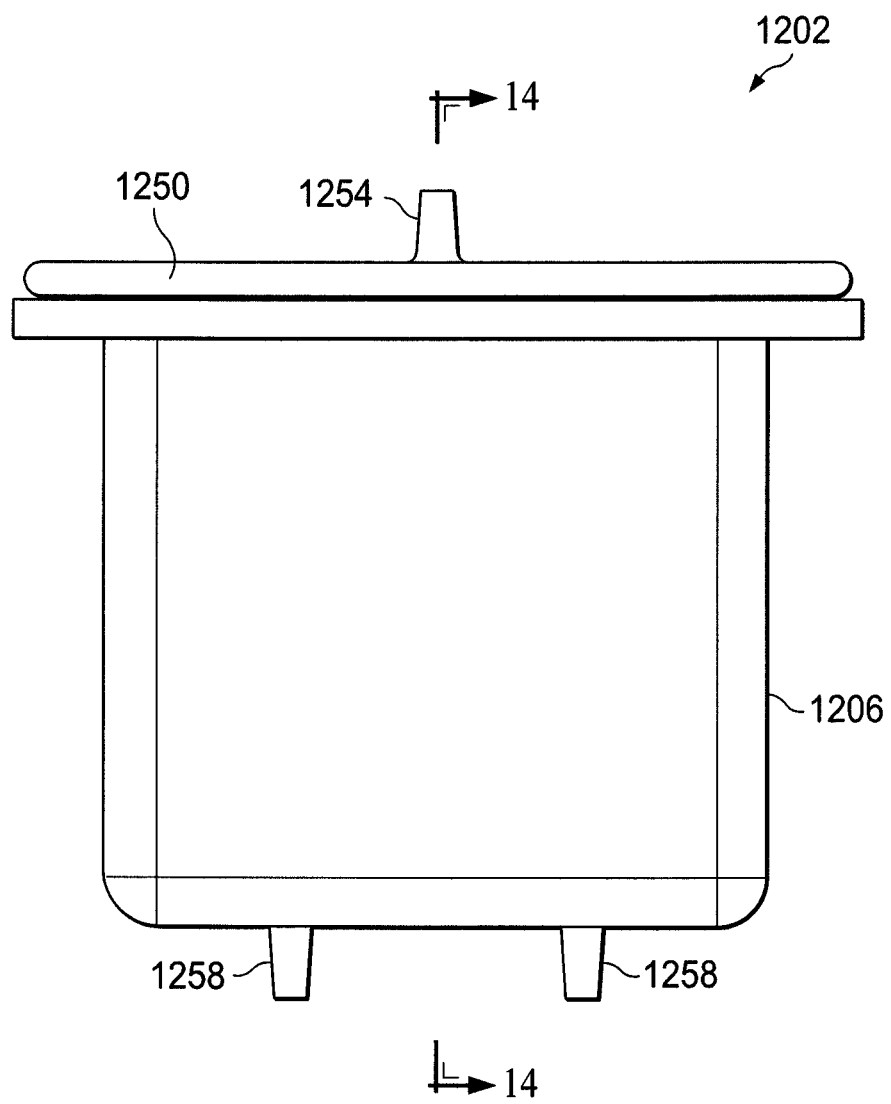
FIG. 13 illustrates an assembled front view of the liquid-collection canister of FIG. 12.
Figure 14:
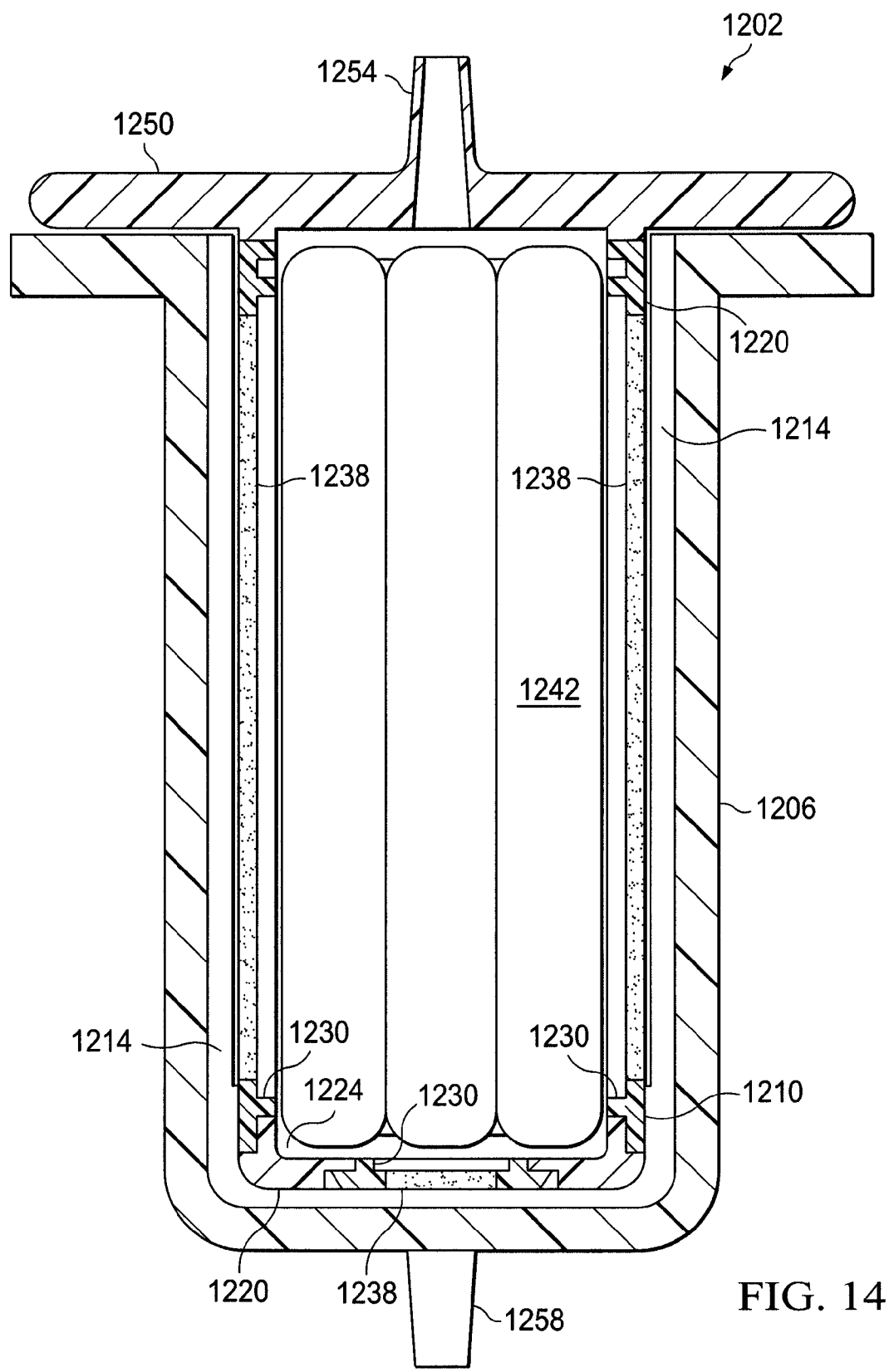
FIG. 14 illustrates a cross-sectional side view of the liquid-collection canister of FIG. 13 taken at 14-14.

Referring to FIGS. 12-14, a liquid collection canister 1202 according to an illustrative embodiment includes an outer shell 1206 and an inner liner 1210 positionable within the outer shell 1206 such that a gas-communication pathway 1214 is created between the inner liner 1210 and the outer shell 1206. In the embodiment illustrated in FIGS. 12-14, the inner liner 1210 includes a plurality of walls 1220 that together define a liquid collection chamber 1224. An aperture 1230 is provided in at least one of the walls 1220, and a liquid-air separator 1238 is positioned over each aperture 1230 to allow the transmission of gases but substantially prevent the transmission of liquids through the liquid-air separator. The liquid-air separators 1238 are similar in function and construction to the liquid-air separators 260, 264, 268, 560, 564 described previously.

Both the inner liner 1210 and the outer shell 1206 may be rectangular-prism shaped, and both are preferably open on one end. A plurality of absorbent pads 1242 may be positioned within the liquid collection chamber 1224. The absorbent pads 1242 are similar in function and construction to the absorbent pads 652 described previously. A lid 1250 is provided to close the open ends of both the inner liner 1210 and the outer shell 1206 when the inner liner 1210 has been inserted within the outer shell 1206. An inlet port 1254 is provided on the lid 1250 to allow fluid connection to a conduit such as conduit 120 of FIG. 1. The inlet port 1254 provides fluid communication between the conduit and the liquid collection chamber 1224. A plurality of outlet ports 1258 (see FIGS. 13 and 14) are provided on the canister 1202 to provide fluid communication with the gas-communication pathway 1214. One of the outlet ports 1258 may be fluidly connected to reduced pressure source such as reduced pressure source 108 described previously. Another of the outlet ports 1258 may be fluidly connected to a pressure sensor for measuring the amount of reduced pressure in the canister 102.

The shape and positioning of the walls 1220 of the inner liner 1210 could vary depending on the shape and size of both the outer shell 1206. In some embodiments, it may be desired to use a stand-alone canister that is not secured to a therapy unit, but rather that is only fluidly connected to a therapy unit or reduced pressure source by a conduit or other pathway. While the walls 1220 of the canister illustrated in FIGS. 12-14 are substantially planar and are arranged substantially perpendicular to adjacent walls, the walls could instead be non-planar and could in some embodiments be positioned at non-perpendicular angles relative to adjacent walls. In another embodiment, a lesser number of walls may be provided such as, for example, in a configuration that includes a cylindrically or spherically shaped wall. In such a configuration, one or more spaces or gas-communication pathways may be formed in the cylindrically or spherically shaped wall.

In the embodiment illustrated in FIGS. 12-14, the gas-communication pathway 1214 is positioned between each of the walls 1220 and the outer shell 1206, and each of the walls 1220 includes at least one of the liquid-air separators 1238. It should be noted that the gas-communication pathway 1214 for a particular wall may be continuous with or in fluid communication with the gas-communication pathways 1214 from other walls. Alternatively, some or all of the gas-communication pathways 1214 may be independent from one another. In one illustrative embodiment, a gas-communication pathway 1214 may not be associated with every wall 1220 of the inner liner 1210. In other embodiments, a gas-communication pathway 1214 is associated with each wall 1220 of the inner liner 1210. If less than all of the walls 1220 are associated with a gas-communication pathway 1214, the walls 1220 having gas-communication pathways may be adjacent one another, or alternatively, opposite one another. In the case of an irregularly-shaped canister, the walls containing gas-communication pathways may not be adjacent or opposite one another. While illustrated in FIGS. 12-14 with only one gas-communication pathway 1214 per wall 1220, multiple, independent spaces or gas-communication pathways could be associated with a particular wall 1220 of the inner liner 1210. Each of the spaces or gas-communication pathways may communicate with a common plenum, such as manifold chamber 624 (see FIG. 8), or the individual gas-communication pathways may be separately ducted to a common conduit or directly to the reduced pressure source. The number of apertures providing fluid communication between a gas-communication pathway and the liquid collection chamber is not strictly limited. In some embodiments, multiple apertures may be provided and spaced apart within the gas-communication pathway to permit more efficient collection and utilization of the liquid collection chamber.

In operation, the liquid collection canister 1202 may be used with a reduced pressure treatment system such as reduced pressure treatment system 100 to collect wound exudate and other liquids drawn from a tissue site by a reduced pressure source. The liquids may travel through a conduit connected between the reduced pressure source and the canister 1202 and into the liquid collection chamber 1224 through the inlet port 1254 of the lid 1250. The liquid collection chamber 1224 of the canister 1202 forms a first space where liquid from the tissue site is collected. The gas-communication pathway or pathways 1214 formed between the inner line 1210 and outer shell 1206 are dry spaces that are substantially protected from liquid by the liquid-air separators 1238. The gas-communication pathway pathways 1214 allow the passage of gas as reduced pressure is applied by the reduced pressure source and gases are drawn from the liquid collection chamber 1224 and the tissue site. As the pressure at the tissue site and within the liquid collection chamber 1224 approach the desired amount of reduced pressure required for reduced pressure treatment or therapy, the flow of gases through the liquid collection chamber 1224 and the gas-communication pathways 1214 is reduced, but liquid may continue to be drawn from the tissue site and collected in the liquid collection chamber 1224.

Figure 15:
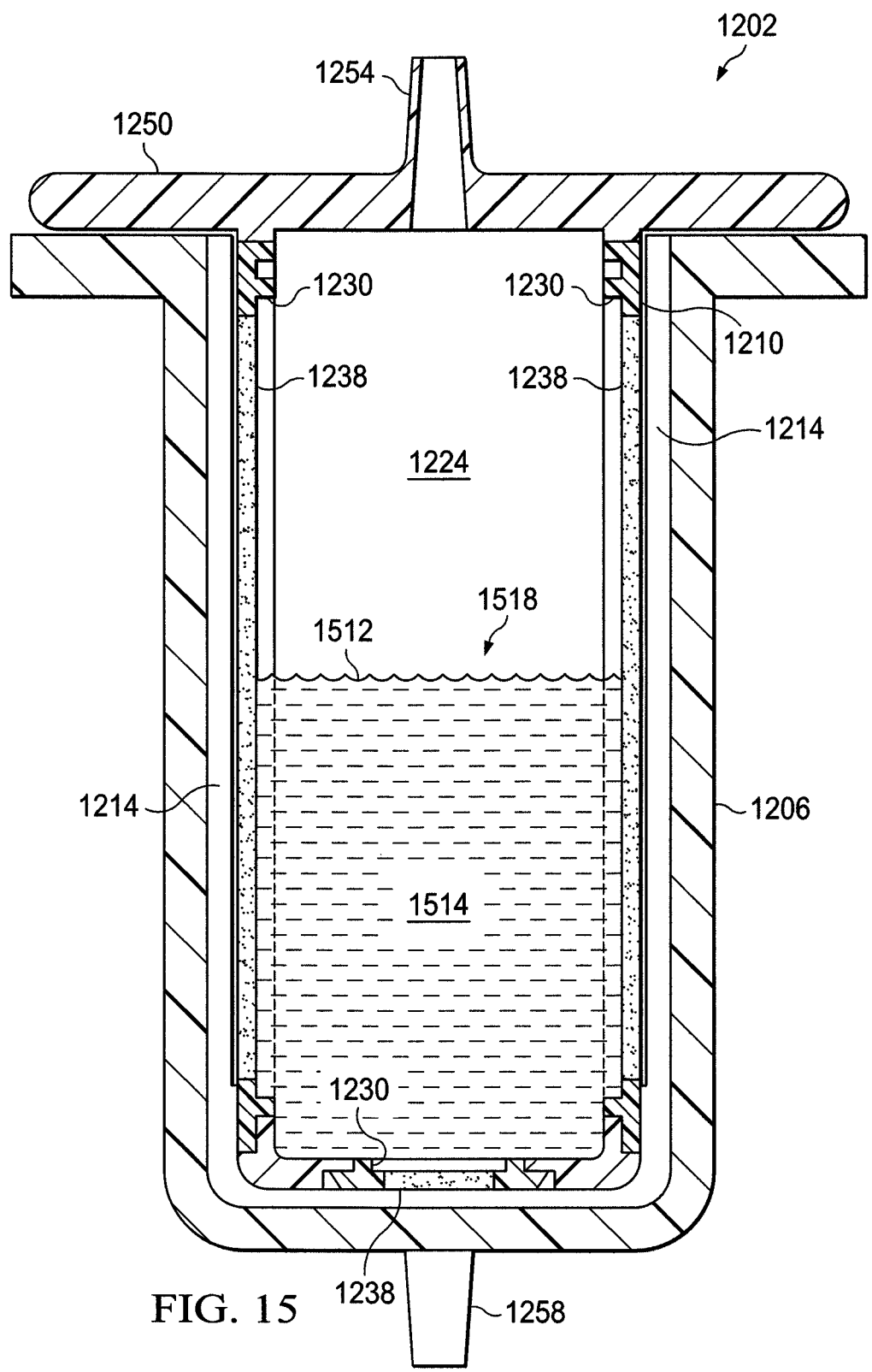
FIG. 15 illustrates a cross-sectional side view of the liquid-collection canister of FIG. 14, the liquid-collection canister shown containing a liquid.

Referring to FIG. 15, which represents a cross-sectional view of the canister 1202 with an orientation similar to that of FIG. 14, a liquid line 1512 represents an upper surface of liquid 1514 that is collected within the liquid collection chamber 1224. As the liquid 1514 fills the liquid collection chamber 1224, the liquid 1514 is substantially prevented from passing through the liquid-air separators 1238 to enter the gas-communication pathway 1214 between inner liner 1210 and outer shell 1206. The surface of the liquid 1514 represented by liquid line 1512 is substantially planar and forms a liquid plane 1518. As the liquid 1514 rises within the canister 1202, any portion of the liquid-air separators 1238 below the surface of the liquid 1514 will no longer allow transmission or flow of gas between the liquid collection chamber 1224 and the gas-communication pathway 1214. In other words, the reduced pressure will no longer be delivered or transferred to the liquid collection chamber 1224 through the portion of the liquid-air separators 1238 that is covered in liquid 1514. In FIG. 15, only the portion of liquid-air separators 1238 above the surface of the liquid 1514 continue to allow gas transmission. As long as a portion of the liquid-air separators 1238 remains uncovered by liquid 1514, that portion of the liquid-air separators 1238 will continue to permit gas flow and transmission of reduced pressure.

Figure 16:
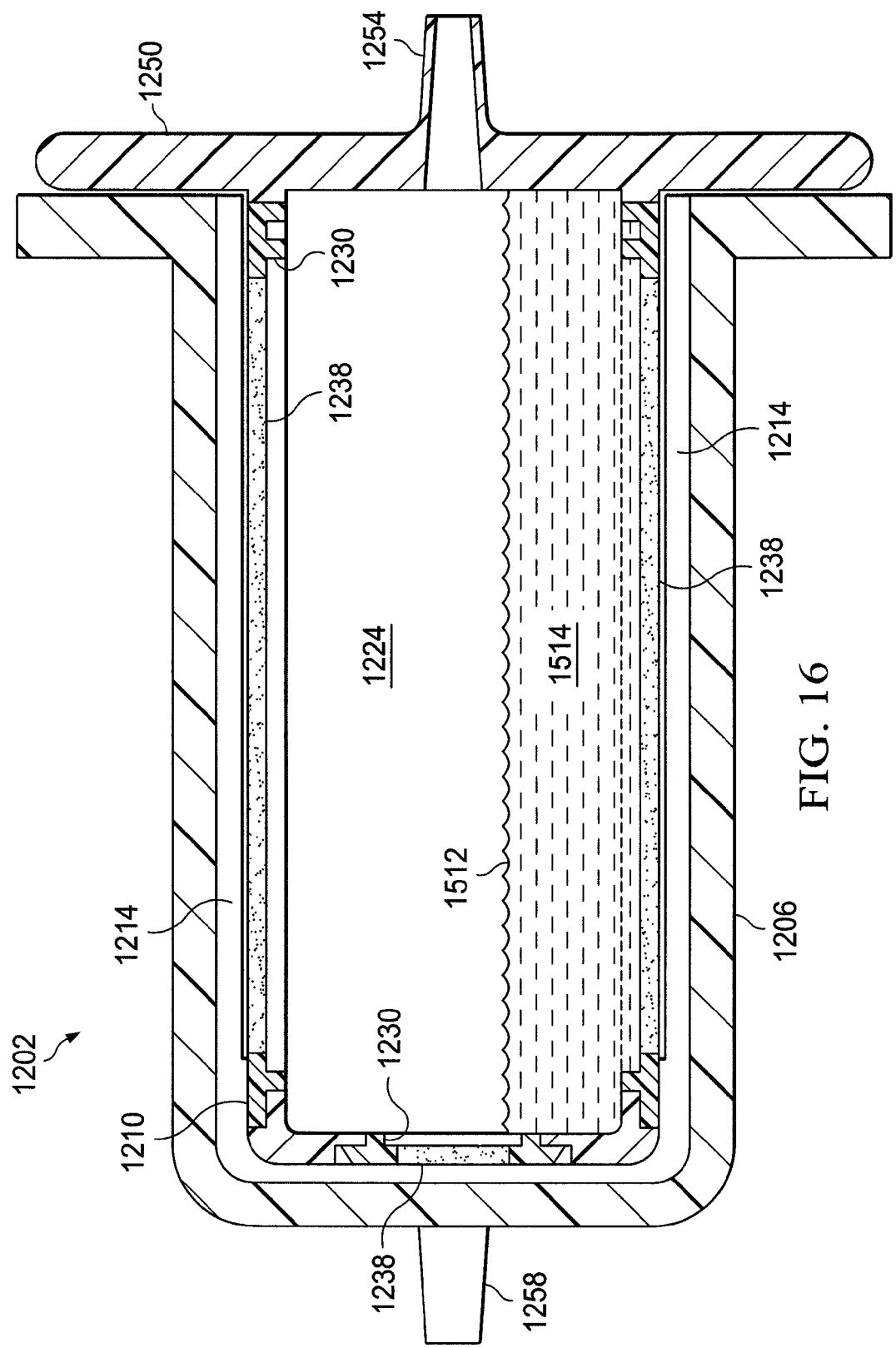
FIG. 16 illustrates a cross-sectional view of the liquid-collection canister of FIG. 15 rotated ninety degrees clockwise.

Referring to FIG. 16, another orientation of the canister 1202 is illustrated similar to the cross-section shown in FIG. 15 but rotated ninety degrees clockwise. In this particular orientation, the liquid-separator 1238 positioned beneath the surface of the liquid 1514 no longer allows gaseous flow between the liquid collection chamber 1224 and the gas-communication pathway 1214. In contrast, the liquid-air separators (or portions thereof) positioned above the surface of the liquid and are capable of allowing gaseous flow.

The reduced pressure treatment systems and liquid-collection canisters described herein may be used as part of a process or method for collecting liquid from a tissue site. In one embodiment, a method of collecting liquid from a tissue site may include applying a reduced pressure to a first gas-communication pathway positioned within a first wall of a canister such as the liquid-collection canisters described with reference to FIGS. 1-16. The reduced pressure is also applied to a second gas-communication pathway positioned within a second wall of the canister. Gaseous flow is allowed between a liquid collection chamber of the canister and the first and second gas-communication pathways to deliver the reduced pressure to the liquid collection chamber. The liquid is drawn into the liquid collection chamber and is substantially prevented from entering the first and second gas-communication pathways.

In another illustrative embodiment, a method of administering reduced pressure treatment to a tissue site includes applying a reduced pressure to a first gas-communication pathway positioned within a first wall of a canister and applying the reduced pressure to a second gas-communication pathway positioned within a second wall of the canister. Gaseous flow is allowed between a liquid collection chamber of the canister and the first and second gas-communication pathways to deliver the reduced pressure to the liquid collection chamber. The reduced pressure is communicated from the liquid collection chamber to the tissue site, and a liquid is drawn from the tissue site into the liquid collection chamber. The liquid is substantially prevented from entering the first and second gas-communication pathways.

It should be apparent from the foregoing that an invention having significant advantages has been provided. While the invention is shown in only a few of its forms, it is not just limited but is susceptible to various changes and modifications without departing from the spirit thereof.

We claim:

1. A system for applying reduced-pressure treatment to a tissue site, the system comprising:
   a liquid collection chamber formed by at least a first wall and a second wall, each wall having an inner surface and an outer surface;
   a first recess formed in the outer surface of the first wall;
   a second recess formed in the outer surface of the second wall;
   a first cover disposed over the first recess to form a first space;
   a second cover disposed over the second recess to form a second space;
   a first aperture disposed in the first wall to fluidly connect the first space and the liquid collection chamber;
   a second aperture disposed in the second wall to fluidly connect the second space and the liquid collection chamber;
   a first liquid-air separator positioned to substantially prevent liquid from the liquid collection chamber from entering the first space through the first aperture of the first wall;
   a second liquid-air separator positioned to substantially prevent liquid from the liquid collection chamber from entering the second space through the second aperture of the second wall;
   a reduced pressure port fluidly connected to the first space and the second space;
   a reduced pressure source in fluid communication with the reduced pressure port; and
   a manifold in fluid communication with the liquid collection chamber and adapted to distribute reduced pressure to the tissue site.

2. The system of claim 1, wherein:
   the first recess comprises a first leg portion intersecting a second leg portion at an apex region of the first recess;
   the first aperture is positioned in the apex region of the first recess;
   the second recess is substantially rectangular in shape and includes a first end and a second end; and
   the second aperture is positioned at the first end of the second recess.

3. The system of claim 2, further comprising:
   a third aperture positioned in the first leg portion of the first recess opposite the apex region;
   a fourth aperture positioned in the second leg portion of the first recess opposite the apex region;
   a fifth aperture positioned at the second end of the second recess;
   a third liquid-air separator positioned to substantially prevent liquid from the liquid collection chamber from entering the first space through the third aperture;
   a fourth liquid-air separator positioned to substantially prevent liquid from the liquid collection chamber from entering the first space through the fourth aperture; and
   a fifth liquid-air separator positioned to substantially prevent liquid from the liquid collection chamber from entering the second space through the fifth aperture.

4. The system of claim 1, further comprising an absorbent pad disposed within the liquid collection chamber.

5. The system of claim 1, further comprising:
   a third aperture disposed in the first wall to fluidly connect the first space and the liquid collection chamber;
   a fourth aperture disposed in the second wall to fluidly connect the second space and the liquid collection chamber;
   a third liquid-air separator positioned to substantially prevent liquid from the liquid collection chamber from entering the first space through the third aperture of the first wall; and
   a fourth liquid-air separator positioned to substantially prevent liquid from the liquid collection chamber from entering the second space through the fourth aperture of the second wall.

6. The system of claim 1, wherein the first wall is opposite the second wall.

7. The system of claim 6, wherein:
   the first recess comprises a first leg portion intersecting a second leg portion at an apex region of the first recess;
   the first aperture is positioned in the apex region of the first recess;
   the second recess is substantially rectangular in shape and includes a first end and a second end;
   the second aperture is positioned at the first end of the second recess.

8. The system of claim 7, further comprising:
   a third aperture positioned in the first leg portion of the first recess opposite the apex region;
   a fourth aperture positioned in the second leg portion of the first recess opposite the apex region;
   a fifth aperture positioned at the second end of the second recess;
   a third liquid-air separator positioned to substantially prevent liquid from the liquid collection chamber from entering the first space through the third aperture;
   a fourth liquid-air separator positioned to substantially prevent liquid from the liquid collection chamber from entering the first space through the fourth aperture; and
   a fifth liquid-air separator positioned to substantially prevent liquid from the liquid collection chamber from entering the second space through the fifth aperture.

* * * * *